United States Patent [19]
Logothetis et al.

[11] Patent Number: 5,250,169
[45] Date of Patent: Oct. 5, 1993

[54] APPARATUS FOR SENSING HYDROCARBONS AND CARBON MONOXIDE

[75] Inventors: Eleftherios M. Logothetis, Birmingham; Richard E. Soltis, Redford, both of Mich.

[73] Assignee: Ford Motor Company, Dearborn, Mich.

[21] Appl. No.: 713,243

[22] Filed: Jun. 7, 1991

[51] Int. Cl.$^5$ .............................................. G01N 27/417
[52] U.S. Cl. .................... 204/424; 204/153.1; 204/153.2; 204/425; 204/426; 422/98; 436/134; 436/139
[58] Field of Search ............................. 204/421–429; 422/98; 436/134, 139

[56] References Cited

U.S. PATENT DOCUMENTS

| | | | |
|---|---|---|---|
| 3,400,054 | 9/1968 | Ruka et al. | 204/427 |
| 4,347,114 | 8/1982 | Kimura et al. | 204/426 |
| 4,505,806 | 3/1985 | Yamada | 204/425 |
| 4,574,627 | 3/1986 | Sakurai et al. | 204/426 |
| 4,753,204 | 6/1988 | Kojima et al. | 123/440 |
| 4,763,628 | 8/1988 | Mieno et al. | 123/440 |
| 4,765,880 | 8/1988 | Hayakawa et al. | 204/425 |
| 4,769,124 | 9/1988 | Okada et al. | 204/425 |
| 4,770,760 | 9/1988 | Noda et al. | 204/425 |
| 4,787,966 | 11/1988 | Nakajima et al. | 204/425 |
| 4,839,018 | 6/1989 | Yamada et al. | 204/425 |
| 4,860,712 | 8/1989 | Nakajima et al. | 204/425 |
| 4,915,813 | 4/1990 | Nakajima et al. | 204/406 |
| 4,922,429 | 5/1990 | Nakajima et al. | 123/489 |
| 5,007,988 | 4/1991 | Archer et al. | 204/424 |
| 5,104,513 | 4/1992 | Lee et al. | 204/425 |

OTHER PUBLICATIONS

E. M. Logothetis "ZrO$_2$ Oxygen Sensors in Automotive Applications" Advances in Ceramics, vol. 3, Science and Technology of Zirconia, copyright 1981 by The American Ceramic Society.

*Primary Examiner*—T. Tung
*Attorney, Agent, or Firm*—Lorraine S. Melotik; Clifford L. Sadler

[57] ABSTRACT

An apparatus and a method for sensing hydrocarbons and carbon monoxide in a measurement gas, e.g., the exhaust gas from an automobile engine. A solid state electrochemical oxygen pumping cell adds oxygen into the apparatus which contains a solid state combustibles sensor for sensing the hydrocarbons and carbon monoxide. The oxygen may be obtained from ambient air or by dissociation of gasses like water present in the measurement gas.

18 Claims, 2 Drawing Sheets

APPARATUS FOR SENSING HYDROCARBONS AND CARBON MONOXIDE

BACKGROUND OF THE INVENTION

1. Field of the Invention

This invention relates to an apparatus for sensing the concentration of hydrocarbons (HC) and carbon monoxide (CO) in a gas which may not contain oxygen, e.g., the exhaust gas from an internal combustion engine, using an apparatus having a sensor which accurately responds to HC and CO only when oxygen is present in the gas.

2. Description of the Related Art

Automotive solid state sensors for on-vehicle measurement of HC and CO in the exhaust gas may be useful for a number of applications such as optimization of engine operation with respect to emission of pollutants (HC, CO and $NO_x$), fuel economy and drivability, detection of cylinder misfires, and monitoring the performance of catalysts used therein. Relatively simple and inexpensive solid state sensors for detection of combustibles including HC and CO are commercially available. These include resistive-type sensors and calorimetric-type sensors.

The resistive-type sensors measure the change in the electrical resistance of an appropriate material as a result of the interaction of the surface of the material with the combustibles. Several different materials including ceramics and polymers have been used for resistive-type sensors. For automotive exhaust applications, however, sensors based on metal oxides are preferable because these materials are more stable and durable in the automotive environment which includes high temperatures, oxidizing and reducing conditions, vibrations and presence of many contaminants. The most popular sensors of this kind are those based on $SnO_2$. In fact, commercial $SnO_2$ devices are made by Figaro Inc. and millions of these sensors are sold worldwide every year. These sensors are generally nonselective, that is, they respond to more than one combustible. However, by appropriate control of additives and sensor microstructure, some degree of selectivity to certain gases may be achieved.

The calorimetric-type sensors measure the rise in the temperature of an appropriate material as the result of the exothermic oxidation of the combustibles on the surface of this material or another material in contact with the first material. Examples of such materials are noble metals such as Pt or Pd. In general, these sensors are also nonselective, although, in some cases, some selectivity may be achieved by filtering or by differential measurements.

The HC and CO sensors of the prior art, however, require the presence of oxygen in the measurement gas for proper device operation. Resistive-type sensors such as $SnO_2$ sensors generally require a large amount of oxygen for stable and reproducible operation. For the calorimetric-type sensors where during operation the HC and CO are oxidized prior to measurement, it is found desirable to provide oxygen in excess of that required for the complete oxidation. This excess of oxygen desirably increases the oxidation efficiency and hence operation of the sensor.

The requirement that oxygen be present in the measurement gas, and generally in excess amounts, for proper operation of these sensors substantially limits the usefulness of these sensors. When an automobile engine is operated with lean air-to-fuel mixtures, the exhaust gas always contains excess oxygen, its concentration increasing with increasing air-to-fuel ratio. On the other hand, when the engine is operated with fuel rich air-to-fuel mixtures, the amount of oxygen in the exhaust gas is very small or essentially nonexistent. Consequently, the sensors of the prior art are of limited usefulness when the air-to-fuel ratio of the engine is varied over a wide range including rich values, unless, for example, oxygen is injected into the exhaust gas as from ambient air. However, it has been found that these sensors operate optimally when a controlled amount of oxygen is provided to the sensor and controlling the amount of ambient air added to the exhaust gas is difficult if not impossible. These are some of the problems that the present invention overcomes.

Advantageously, this invention comprises an apparatus which contains one of these combustibles sensors yet can measure HC and CO in the exhaust gas even when it does not contain oxygen. This apparatus is thus able to operate accurately to measure HC and CO in exhaust gas under all engine operating conditions, from very rich air-to-fuel mixtures (absence of oxygen) to very lean air-to-fuel mixtures (abundance of oxygen) without adding ambient air to the exhaust gas but by pumping an amount of oxygen into the apparatus. According to the present invention, this oxygen can be added to the sensor in precisely controlled amounts. The present invention apparatus thus overcomes deficiencies of prior art sensors.

SUMMARY OF THE INVENTION

This invention is directed to an apparatus for measuring hydrocarbons and carbon monoxide in a measurement gas. The apparatus includes a solid state electrochemical oxygen pumping cell having an electrode layer on each of two opposite sides of an oxygen-ion conducting solid electrolyte member. It further includes a supporting structure which together with the solid state electrochemical oxygen pumping cell defines a volume, one electrode layer of the cell being inside the volume and the other electrode layer being exposed to another gas outside the volume. During operation of the apparatus, the electrochemical oxygen pumping cell is capable of providing oxygen into the volume. The supporting structure has an aperture for providing communication between the volume and the measurement gas present outside the volume. A sensor means is also included mounted within the volume for generating an output signal indicative of the amount of hydrocarbons and carbon monoxide present in the measurement gas. The other gas outside the volume that the other electrode is exposed to may be, e.g., the measurement gas or ambient air. A heater may be included with the apparatus for heating the apparatus. Various embodiments of such an apparatus are described in detail herein.

According to another embodiment of the invention, it comprises an integrated-film apparatus including in order: a supporting solid substrate; a sensor means comprising two metal film electrodes spaced apart and deposited on one side of the substrate and a hydrocarbon and carbon monoxide sensitive film deposited to cover a portion of the substrate between the electrodes and contacting both electrodes; a porous inert layer deposited to substantially cover the entire substrate side carrying the sensor means; a gas impermeable film deposited on a part of the porous layer located over the area of the film so as to form a volume with the substrate; a first porous conducting electrode deposited on a portion of the porous layer that is not covered by the gas impermeable film; a gas impermeable, oxygen-ion conducting solid electrolyte layer; a second porous conducting electrode deposited on the solid electrolyte layer substantially above the first porous conducting electrode. The first porous conducting electrode layer, the solid electrolyte layer, and the second porous conducting electrode layer form an electrochemical oxygen pumping cell for providing oxygen into the porous inert layer.

The invention is also directed to a method for sensing hydrocarbons and carbon monoxide in a measurement gas including the steps of: introducing the measurement gas into a volume while also adding oxygen into the volume by means of a solid state electrochemical oxygen pumping cell, measuring the concentration of the hydrocarbons and the carbon monoxide in the volume with a sensor means positioned within the volume and capable of generating an output signal indicative of the hydrocarbons and the carbon monoxide therein.

Advantageously, the present invention apparatus can provide oxygen into the apparatus from ambient air or from the exhaust gas itself by dissociation. Further, it can provide the oxygen in precisely controlled amounts as may be desired.

DETAILED DESCRIPTION OF THE PREFERRED EMBODIMENTS

Figure 1:
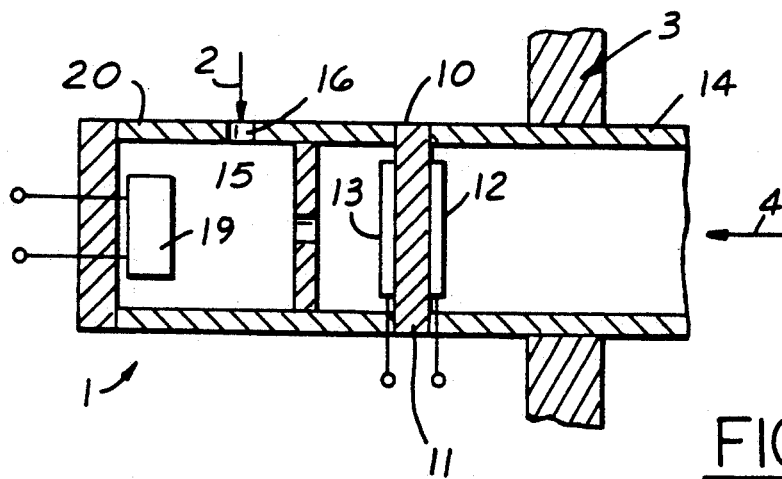
FIG. 1 is a schematic of a first embodiment of an apparatus in accordance with this invention.

Referring to FIG. 1, an apparatus 1 according to one of the embodiments of the present invention is shown to be partially inserted into a measurement gas 2 through a wall 3 which is one of the walls separating the measurement gas from the ambient air 4. The measurement gas 2 typically contains CO and HC and inert gases such as nitrogen ($N_2$). The measurement gas may also contain oxygen. In particular, when the measurement gas is the exhaust gas from an internal combustion engine, it generally contains varying amounts of $N_2$, $CO_2$, $H_2O$, CO, $H_2$, $NO_x$, and various hydrocarbons as the main gas constituents. The exhaust gas may also contain oxygen. As shown, wall 3 is, for example, the wall of the exhaust pipe connected to the exhaust manifold of the engine. The apparatus supporting structure 20 defines, in part, a volume 15 which communicates with the measurement gas 2 (e.g., the exhaust gas) through an aperture 16. A sensor 19 for HC and CO, e.g., a resistive-type or a calorimetric-type sensor is placed inside volume 15 and is used to measure the concentration of HC and CO inside volume 15. In operation, it does so by generating an output signal indicative of the amount of hydrocarbons and carbon monoxide present in the measurement gas. The device also includes a means for providing a desired concentration of oxygen inside volume 15. The means for providing oxygen into the volume 15 of the apparatus is a solid state electrochemical oxygen pumping cell 10 attached to the apparatus structure 20, cell 10 further defining (in combination with supporting structure 20) volume 15. The cell 10 is also attached to a housing 14 which serves as a means for mounting apparatus 1 to the wall 3 and provides access, if desired, of ambient air 4 to cell 10.

Electrochemical cell 10 may consist of a piece of an oxygen-ion conducting solid electrolyte 11 such as yttria-doped $ZrO_2$ and two porous electrodes 12 and 13, one on each side of the solid electrolyte 11. Electrodes 12 and 13 are made according to the well-established art of solid electrolyte oxygen sensors used, for example, extensively for air-to-fuel control of internal combustion engines. For example, electrodes 12 and 13 may be porous platinum layers deposited by thick film techniques. Electrode 12 is exposed to the ambient air 4 whereas electrode 13 is exposed to volume 15 of apparatus 1. Housings 14 and supporting structure 20 may be made from inert materials such as alumina or from the same material as the solid electrochemical cell (e.g., $ZrO_2$).

Apparatus 1 is generally provided with a heater to maintain the various elements of apparatus 1 at desired temperatures which may be the same for all elements. For example, when the combustibles sensor 19 is a $SnO_2$-based sensor, a temperature in the range 300° to 400° C. is desirable. Depending on the type of the material and the dimensions of the electrolyte 11, the above range of temperatures may also be sufficient for proper operation of cell 10. A generally useful temperature range for the apparatus during operation is between about 200° C. and 800° C.

In operation, portion of the measurement gas 2 (exhaust gas) enters volume 15 of apparatus 1 by diffusion through aperture 16. A current I is sent through electrochemical cell 10 in the direction so that electrode 12 is negative and electrode 13 is positive. The electrical current causes oxygen to be transferred (pumped) from the air 4 into volume 15. The rate of oxygen transfer is proportional to the current. The measurement gas entering apparatus 1 through aperture 16 is mixed in volume 15 with the oxygen pumped into volume 15 by the electrochemical cell 10. By choosing a sufficiently large current I passing though the cell 10, a sufficient concentration of oxygen can always be maintained inside volume 15 even for the most fuel rich air-to-fuel mixtures. Consequently, the HC and CO inside volume 15 can be accurately measured by sensor 19. It is well known in the art that the amount of oxygen which may be pumped by an electrochemical oxygen pumping cell increases with increasing I. Thus by changing the current, the amount of oxygen pumped into volume 15 can be varied. In operation, apparatus 1 is equipped with appropriate electronics for the oxygen pumping with cell 10 and for the operation of sensor 19.

Advantageously in detecting HC and CO in the exhaust from an engine, access to the ambient air shown in the embodiment of FIG. 1 is not necessary. The exhaust contains large amounts of $CO_2$ and $H_2O$ which can act as sources of oxygen. The sensor of FIG. 1 may be modified to provide electrode layer 12 access to the measurement gas. For example, housing 14 can be eliminated and the apparatus completely immersed in the measurement gas (exhaust). By applying a voltage V in excess of 1.2 volts with the proper polarity across cell 10, oxygen is pumped into volume 15 by electrodissociation at electrode 12 of $CO_2$ and $H_2O$ molecules from the exhaust gas adjacent to electrode 12.

Various modifications of the configuration of apparatus 1 and refinements of the operation of apparatus 1 are possible. For example, a partial barrier 17 to the diffusion of oxygen may be placed inside volume 15 between the pump cell 10 and the combustible-sensor-19/aperture-16 combination. This partial barrier may be, for example, in the form of a wall with an opening. The addition of this barrier to the apparatus structure could be helpful in eliminating possible reaction of the oxygen with the HC or CO on the surface of the electrode of the cell inside volume 15.

Figure 2:
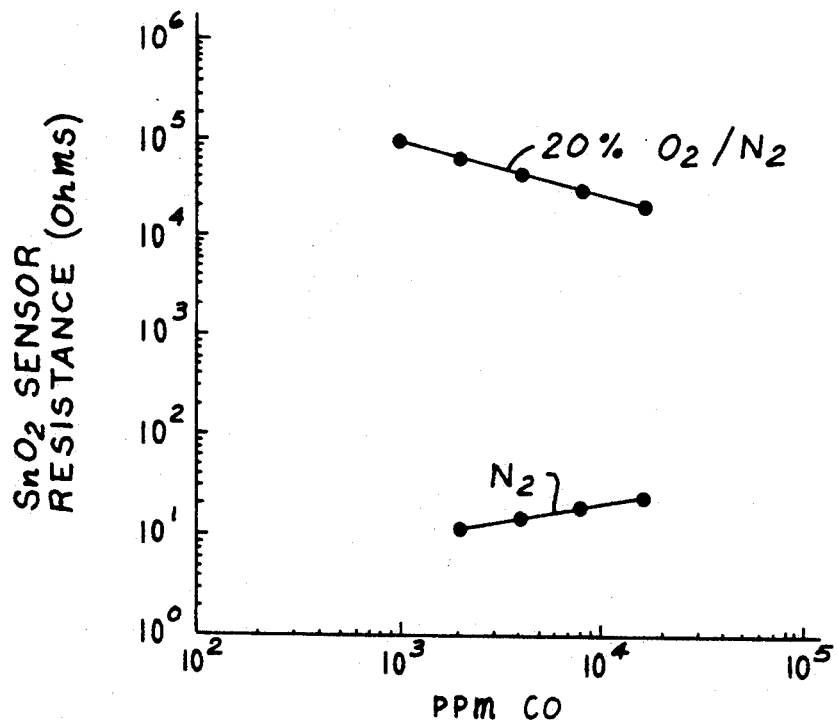
FIG. 2 shows the response to CO of an apparatus according to the present invention in the absence of oxygen (CO/$N_2$ mixtures) and when oxygen is added to the CO/$N_2$ mixtures.

FIG. 2 shows results of laboratory measurements which demonstrate the operation of the apparatus of this invention. In these measurements, a commercial resistive-type $SnO_2$ sensor was used as the combustibles sensor 19. In the absence of oxygen, the resistance of the $SnO_2$ sensor 19 for CO in $N_2$ (FIG. 2, lower curve) is orders of magnitude smaller than for CO in air. When oxygen is introduced into the apparatus structure, however, the resistance shows the expected response to varying concentrations of CO (FIG. 2, upper curve). Similar results are obtained with hydrocarbons such as propane and methane.

As another example of an alternative embodiment of the invention, housing 20 may have an optional rear opening (not shown in the FIG.) which permits the gas to pass through the apparatus structure. In the embodiment of FIG. 1 where the portion of the measurement gas enters the apparatus structure by diffusion through aperture 16, the rear opening is not needed. If the apparatus is heated and placed in a position so that the rear part of the apparatus is at higher temperature than the front part, then the gas is driven by convection through apparatus 1 from the front aperture 16 to the rear opening provided that a rear opening exists. If housing 20 of apparatus 1 forms a section of the gas flow vessel so that all the measurement gas flows through the aperture 16, then the rear opening is clearly needed.

As still another embodiment of the apparatus of the present invention, the apparatus may be modified to always pump sufficient oxygen into volume 15 so that the concentration of oxygen in the volume is maintained at a constant value. Keeping the oxygen in excess at a prescribed constant value may be desirable in order to optimize the operation of sensor 19. This desired action may be accomplished by adding another solid state electrochemical cell (e.g., of $ZrO_2$), acting here as an oxygen sensing cell, having one electrode facing volume 15 and the other facing the ambient air as a reference. The open circuit voltage (emf) developed across this oxygen sensing cell because of the difference in the oxygen partial pressure at the two electrodes of the cell, provides a measure of the concentration of oxygen inside volume 15. Oxygen sensing cells are well known in the art. During operation, the pumping current through cell 10 is adjusted to keep the emf of the oxygen sensing cell at a constant value. This assures that the oxygen in the volume 15 is constantly maintained in excess at a chosen concentration. U.S. Pat. Nos. 4,272,329; 4,272,330; and 4,272,231 to Hetrick et al teach employing an oxygen sensing cell in combination with an oxygen pumping cell to maintain a constant oxygen concentration, which references are hereby expressly incorporated for such teachings.

The main function of the electrochemical oxygen pumping cell 10 is to add the oxygen needed for the operation of combustibles sensor 19. It is, of course, possible, to add oxygen by other means. For example, an electrically actuated valve could be used to admit ambient air into the exhaust gas. The apparatus then becomes bulky and the amount of oxygen introduced into volume 15 can not be easily controlled. Alternatively, cell 20 may be replaced with a porous material which allows a certain flux of air to enter volume 15. In this case, the amount of oxygen introduced into volume 15 can not be varied or turned off.

The present invention, on the other hand advantageously allows for the precisely controlled addition of oxygen into volume 15 by means of the electrochemical oxygen pumping cell. This oxygen can be obtained from ambient air as shown in FIG. 1. The use of an electrochemical oxygen pumping cell in the invention apparatus advantageously eliminates the need to use ambient air as the source of the oxygen. The oxygen can be produced from the dissociation of water and carbon dioxide always present in the exhaust gas as described above. This allows for more flexibility in the use of the apparatus since it does not have to be provided with access to ambient air. Still further, when the oxygen pumping cell is used in combination with an oxygen sensing cell as described above, the concentration of oxygen provided in volume 15 may be maintained at a constant level for optimum performance as is necessary for certain types of combustibles sensors.

Figure 3:
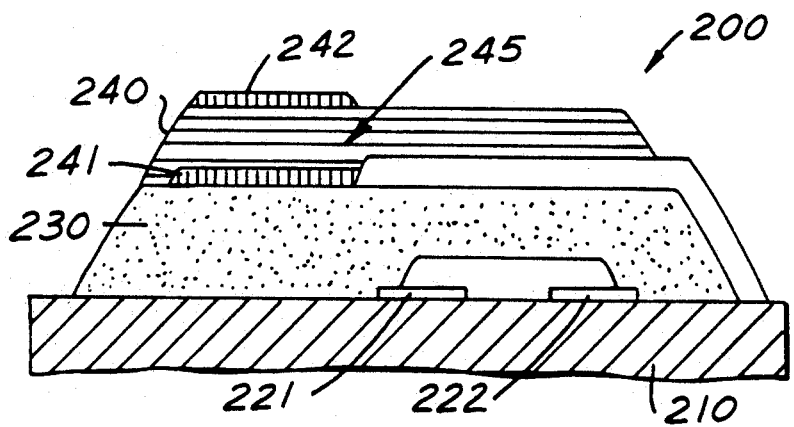
FIG. 3 is a schematic of a second embodiment of an apparatus in accordance with this invention.

FIG. 3 shows a second embodiment of the present invention. The apparatus 200 shown in this figure is an integrated film-type version of the apparatus of FIG. 1 and includes a HC and CO combustibles sensor 220, and an electrochemical oxygen pumping cell 240. A substrate 210 acts as a support for apparatus 200 and is typically made of a material such as aluminum oxide. Two metal film electrodes 221 and 222 made, for example, from gold or platinum, are deposited on substrate 210 and a metal oxide film of, e.g., $SnO_2$ or ZnO is deposited on top the electrodes to form the HC and CO combustibles sensor 220. A porous layer made from an inert material such as alumina or spinel or $ZrO_2$ is deposited directly on sensor 220 and part of substrate 210 to form an integrated volume 230. The part of the porous layer 230 that is over the sensor 220 is covered with a gas impermeable film 235 made from inert materials such as glass, alumina or quartz. A porous electrode 241 made, e.g., of platinum is deposited on top of the exposed part of the porous layer 230. A dense solid electrolyte (e.g., Y-doped $ZrO_2$) layer 245 is deposited on top of electrode 241 (and inert layer 235). Finally a second porous platinum electrode 242 is deposited on top of solid electrolyte layer 245. Solid electrolyte layer 245 and platinum electrodes 241 and 242 form electrochemical oxygen pumping cell 240. In operation, a voltage applied across cell 240 transfers oxygen into the porous layer 230 from oxygen which may be present in the exhaust gas or from dissociation of $CO_2$ and $H_2O$ present in the exhaust gas. This oxygen transferred into layer 230 mixes with the species contained in the measurement gas which diffuses into porous layer 230 through the exposed portion of the porous layer 230. Since excess oxygen can be maintained within layer 230, the HC and CO contained in the measurement gas can be accurately measured by sensor 220.

Figure 4:
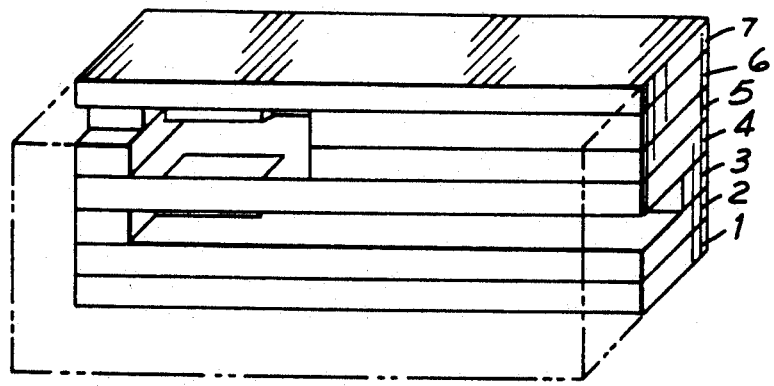
FIG. 4 is a schematic of a third embodiment of this invention made by laminating ceramic plates to form a planar apparatus.
Figure 5:
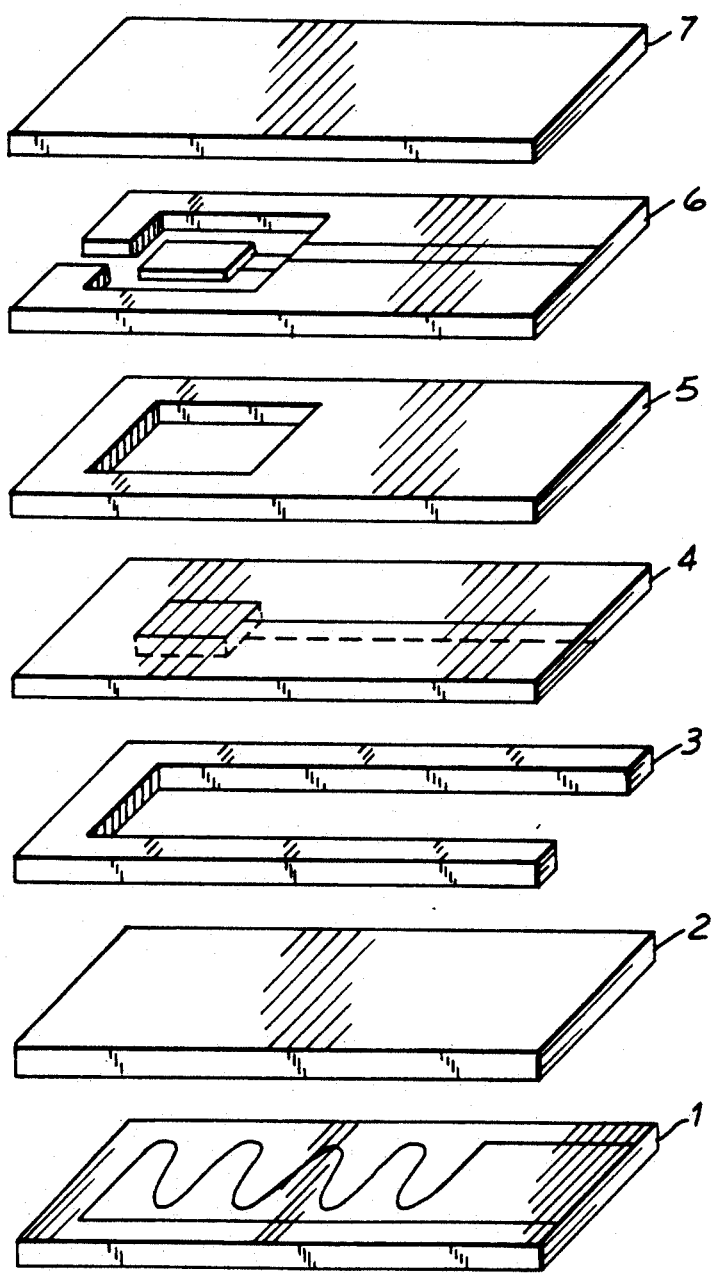
FIG. 5 is an exploded perspective view of the apparatus of FIG. 4 showing the structure of each ceramic sheet.

FIG. 4 shows an embodiment of the present invention in the form of a planar apparatus made by laminating and co-firing ceramic sheets. FIG. 5 is an exploded perspective view of the apparatus of FIG. 4 showing the various ceramic sheets. Ceramic sheet 4 is made from an oxygen-ion conducting solid electrolyte such as Y-doped $ZrO_2$. The other sheets can be made also from $ZrO_2$ or from other inert structural ceramic materials such as alumina. Sheet 1 includes a heater which is, for example, screen-printed on sheet 1. Sheet 2 is a solid plate whereas sheet 3 is in the form of a U-shaped spacer. Sheet 3 could be reversed so that its opening is on the same end of the apparatus as the aperture of sheet 6 if, e.g., the apparatus will provide oxygen from the exhaust gas by dissociation of water and carbon dioxide. Sheet 4, made from Y-doped $ZrO_2$, has printed porous electrodes (e.g., of platinum) one on each side to form an electrochemical oxygen pumping cell. Sheets 2, 3 and 4 form a structure which, according to this embodiment, is connected to the ambient air. Sheet 5 defines, in part, a volume which is in direct communication with the volume defined by sheet 6. A HC/CO sensor such as a resistive-type $SnO_2$ sensor is mounted inside this volume. Finally, sheet 7 is a solid plate which seals the upper part of the apparatus from the measurement gas. Optionally, a second heater similar to sheet 1 may be laminated on top of sheet 7. As an alternative, the HC/CO sensor may be replaced with a film-type $SnO_2$ sensor deposited on the side of sheet 7 facing sheet 6. In such a case, sheet 5 would not be necessary.

Additional modifications and variations will no doubt occur to those skilled in the various arts to which this invention pertains. For example, the shape and relative size of the various components of the present apparatus may be varied from the ones disclosed here. The resistive-type $SnO_2$ sensor shown in FIGS. 2, 3 and 4 may be replaced by a calorimetric-type sensor or other suitable sensor. These and all other variations which basically rely on the teachings through which this disclosure has advanced the art are properly considered within the scope of this invention.

We claim:

1. An apparatus for measuring hydrocarbons and carbon monoxide in a measurement gas comprising:
   a solid state electrochemical oxygen pumping cell comprising a porous electrode layer on each of two opposite sides of an oxygen-ion conducting solid electrolyte member;
   a supporting structure which together with said solid state electrochemical oxygen pumping cell substantially defines a volume, one electrode layer of said cell being inside said volume and the other electrode layer being exposed to another gas outside said volume and during operation of said apparatus said electrochemical oxygen pumping cell being capable of providing oxygen into said volume;
   an aperture in said supporting structure for providing communication between said volume and said measurement gas present outside said volume; and
   a solid state combustibles sensor means mounted within said volume for generating an output signal indicative of the amount of hydrocarbons and carbon monoxide present in said measurement gas.

2. The apparatus according to claim 1 wherein said apparatus further comprises a heater for heating said apparatus.

3. The apparatus according to claim 2 wherein said heater maintains said apparatus at a temperature in the range of 200° to 800° C.

4. The apparatus according to claim 1 further comprising a partial barrier to the diffusion of oxygen partially separating said electrochemical cell from said combustibles sensor and said aperture.

5. The apparatus according to claim 4 wherein the partial barrier is a wall with an opening.

6. The apparatus according to claim 1 wherein said solid state combustibles sensor means comprises a $SnO_2$ sensor.

7. The apparatus according to claim 1 wherein said another gas is said measurement gas.

8. The apparatus according to claim 1 wherein said another gas is ambient air.

9. The apparatus according to claim 1 which further comprises an electrochemical oxygen sensing cell employed in combination with said electrochemical oxygen pumping cell to measure the concentration of said oxygen within said volume and maintain it at a desired level.

10. The apparatus according to claim 1 wherein said solid state electrochromic oxygen pumping cell and said solid state combustibles sensor means are formed as one integrated laminated planar apparatus.

11. The apparatus of claim 10 wherein said solid state combustibles sensor means comprises a $SnO_2$ sensor.

12. An integrated-film apparatus for measuring hydrocarbons and carbon monoxide in a measurement gas comprising in order:
    a supporting solid substrate;
    two metal film electrodes spaced apart and deposited on one side of said substrate;
    a sensor means comprising a continuous hydrocarbon and carbon monoxide sensitive film deposited to cover a portion of each of said electrodes and a portion of said substrate between said electrodes;
    a porous inert layer deposited to substantially cover the entire substrate side carrying said sensor means;
    a gas impermeable film deposited on a part of the porous layer located over the area of said film so as to form a volume with said substrate;
    a first porous conducting electrode deposited on a portion of the porous layer that is not covered by said gas impermeable film;
    a gas impermeable, oxygen-ion conducting solid electrolyte layer;
    a second porous conducting electrode deposited on said solid electrolyte layer substantially above said first said porous conducting electrode; and
    wherein said first porous conducting electrode, said solid electrolyte layer, and said second porous conducting electrode form an electrochemical oxygen pumping cell for providing oxygen into said porous inert layer.

13. The apparatus according to claim 12 wherein said substrate is alumina and said porous layer is spinel or alumina.

14. The apparatus according to claim 12 wherein said hydrocarbon and carbon monoxide sensitive film is $SnO_2$.

15. The apparatus according to claim 12 wherein said gas impermeable layer is selected from the group comprising glass, alumina, and quartz.

16. The apparatus according to claim 12 wherein said first and second porous electrodes are made of platinum.

17. The apparatus according to claim 12 wherein said solid electrolyte is Y-doped $ZrO_2$.

18. The apparatus according to claim 12 wherein the measurement gas is the exhaust from an internal combustion engine.

* * * * *